(12) United States Patent
Chen et al.

(10) Patent No.: US 9,119,567 B2
(45) Date of Patent: Sep. 1, 2015

(54) METHODS AND APPARATUS FOR DETECTING A FALL OF USER

(75) Inventors: Ningjiang Chen, Shanghai (CN); Sheng Jin, Shanghai (CN)

(73) Assignee: Koninklijke Philips N.V., Eindhoven (NL)

( * ) Notice: Subject to any disclaimer, the term of this patent is extended or adjusted under 35 U.S.C. 154(b) by 693 days.

(21) Appl. No.: 13/320,463

(22) PCT Filed: Jun. 8, 2010

(86) PCT No.: PCT/IB2010/052525
§ 371 (c)(1),
(2), (4) Date: Nov. 14, 2011

(87) PCT Pub. No.: WO2010/150117
PCT Pub. Date: Dec. 29, 2010

(65) Prior Publication Data
US 2012/0065925 A1 Mar. 15, 2012

(30) Foreign Application Priority Data
Jun. 23, 2009 (CN) .......................... 2009 1 0150845

(51) Int. Cl.
*A61B 5/11* (2006.01)
*G01L 11/00* (2006.01)
*G06F 17/40* (2006.01)
*G06F 19/00* (2011.01)

(52) U.S. Cl.
CPC .............. *A61B 5/1117* (2013.01); *G01L 11/004* (2013.01); *G06F 17/40* (2013.01); *G06F 19/00* (2013.01)

(58) Field of Classification Search
CPC ...... A61B 5/00; A61B 5/0002; A61B 5/0015; A61B 5/0024; A61B 5/103; A61B 5/11; A61B 5/1116; A61B 5/1117; G01D 7/00; G01D 9/00; G01D 21/00; G01L 9/00; G01L 9/08; G01L 11/00; G01L 11/004; G01L 19/00;G01L 19/02; G06F 11/00; G06F 11/30; G06F 11/32; G06F 11/34; G06F 15/00; G06F 15/16; G06F 17/00; G06F 17/10; G06F 17/40; G06F 19/00
USPC ................. 73/1.01, 1.57, 37, 170.016, 432.1, 73/865.8, 865.9, 866.3; 324/71.1; 702/1, 702/2, 3, 22, 40, 74, 87, 104, 127, 138, 150, 702/182, 187, 189; 708/100, 105, 200
See application file for complete search history.

(56) References Cited

U.S. PATENT DOCUMENTS 8,381,603 B2 * 2/2013 Peng et al. ................... 73/865.4
2010/0052896 A1 3/2010 Goodman
(Continued)

FOREIGN PATENT DOCUMENTS

| DE | 10200705258 A1 | 5/2009 |
|----|----------------|--------|
| EP | 1642248 B1 | 3/2007 |
| WO | 2010037564 A1 | 4/2010 |

OTHER PUBLICATIONS

Wilson, "Pressure Measurement: Principles and Practice", Sensors, Apr. 29, 2009, pp. 1-9.

*Primary Examiner* — Edward Cosimano

(57) ABSTRACT

This invention relates to methods and apparatus for detecting a fall of a user, especially to methods and apparatus for detecting a fall of a user by using pressure sensors. This invention discloses an apparatus for detecting a fall of a user, and the apparatus comprises first and second pressure sensors configured to obtain first and second data values of atmosphere pressure and intended to be worn on the body of the user, and a processor configured to derive a third data value of atmosphere pressure for determining whether a fall occurs or not from the first and second data values of atmosphere pressure. The first and second pressure sensors are configured in a way such that preset orientations of the first and second pressure sensors are opposite to each other. In this way, the weight of measuring elements comprised in the first and second pressure sensors have opposite effects on the measured atmosphere pressure, and thus (?) the measurement error caused by pressure sensor orientation variation can be reduced or even eliminated.

20 Claims, 10 Drawing Sheets

(56) References Cited

U.S. PATENT DOCUMENTS

2011/0162433 A1\* 7/2011 Peng et al. .................... 73/1.13
2011/0246114 A1\* 10/2011 Jin ................................. 702/94
2012/0016270 A1 1/2012 Buhler et al.

\* cited by examiner

METHODS AND APPARATUS FOR DETECTING A FALL OF USER

FIELD OF THE INVENTION

The invention relates to methods and apparatus for detecting a fall of a user, especially to methods and apparatus for detecting a fall of a user by using pressure sensors.

BACKGROUND OF THE INVENTION

Many people are at increased risk of injury or death as a result of a chronic health condition or complications resulting from acute illness, disability, or advancing age. Many other people suffer from chronic, or at least sustained, conditions that require long term treatment. Other people, such as soldiers, police, fire fighters, rescue workers, etc., work under hazardous and life-threatening conditions. In many instances, detecting a fall of these individuals is necessary to render aid when needed to prevent further health issues that could result from a fall.

Monitoring altitude change of a wearable fall detecting apparatus can detect a fall of a user. Usually, the altitude of a fall detecting apparatus worn at the neck of the user will change about 60 cm when a fall occurs. Therefore, whether a fall occurs or not can be detected by checking the altitude change of the fall detecting apparatus. To obtain the altitude change of the fall detecting apparatus, a pressure sensor is a good candidate sensor that can measure atmosphere pressure, which can be converted into an altitude value.

When the altitude value is taken into consideration for detecting a fall, it would be better to have a pressure sensor that can obtain an altitude value with a resolution of about 10 cm, allowing a fall to be detected correctly without a false dismissal or a false alarm. However, a pressure sensor cannot fulfill the resolution requirement of 10 cm when the pressure sensor's orientation varies.

FIG. 1 illustrates a schematic diagram of a pressure sensor SCP1000-D01 produced by VTI Technologies, and FIG. 1 (b) illustrates measured altitude values vs real altitude values when the orientation of the pressure sensor varies. The dashed line with triangles corresponds to the situation when the pressure sensor's surface with the text "D01" is vertical to the ground; the solid line with squares corresponds to the situation when the pressure sensor's surface with the text "D01" faces upward; and the dash-dot line with diamonds corresponds to the situation when the pressure sensor's surface with the text "D01" faces downward.

Referring to FIG. 1 (b), the pressure sensor may obtain an altitude variation value with an error of 50 cm if the pressure sensor's surface with the text "D01" turns from upward to downward. In fall detection applications, an altitude value with an error of 50 cm cannot be accepted because it will generate a false dismissal or a false alarm. The reason for an error of the altitude value is that the atmosphere pressure is measured by detecting the deformation, in response to the atmosphere pressure, of a pressure sensing element comprised in the pressure sensor, and the weight of the pressure sensing element affects the deformation of the pressure sensing element when the pressure sensor's orientation varies. In addition, a protective gel is provided on the pressure sensing element to protect the pressure sensing element from moisture, and the weight of the protective gel also affects the deformation of the pressure sensing element.

SUMMARY OF THE INVENTION

Considering the error in altitude value brought by the error in atmosphere pressure caused by the pressure sensor orientation variation mentioned above, it would be advantageous to reduce or eliminate the error in atmosphere pressure measured by the pressure sensor to improve fall detection accuracy.

To better address one or more of the above concerns, in a first aspect of the present invention, there is provided an apparatus for detecting a fall of a user, the apparatus comprising:

first and second pressure sensors configured to obtain first and second data values of atmosphere pressure and intended to be worn on the body of the user; and a processor configured to derive a third data value of atmosphere pressure for determining whether a fall occurs or not from the first and second data values of atmosphere pressure;

wherein the first and second pressure sensors are configured in a way such that preset orientations of the first and second pressure sensors are opposite to each other.

The preset orientations can be determined in many ways, such as on the basis of the appearance or the structure of the pressure sensors. Since the preset orientations of the first and second pressure sensors are configured so as to be opposite to each other, the weight of measuring elements comprised in the first and second pressure sensors have opposite effects on the measured atmosphere pressure. Therefore, the error of the measured atmosphere pressure caused by pressure sensor orientation variation can be compensated by deriving the third data value of atmosphere pressure from the first and second data values of atmosphere pressure obtained by the first and second pressure sensors.

In a second aspect of the present invention, there is provided a pressure sensor for measuring atmosphere pressure, the pressure sensor comprising:

first and second pressure sensing elements configured to obtain first and second data values of atmosphere pressure; and a processor configured to derive a third data value of atmosphere pressure from the first and second data values of atmosphere pressure;

wherein each pressure sensing element is deformable in response to the atmosphere pressure and comprises an atmosphere pressure sensing surface, and the normal direction of the atmosphere pressure sensing surface of the first pressure sensing element is configured so as to be opposite to the normal direction of the atmosphere pressure sensing surface of the second pressure sensing element.

Since the atmosphere pressure sensing surfaces of the first and second pressure sensing elements face in opposite directions, the weight of the first and of the second pressure sensing elements have opposite effects on the deformation of the first and second pressure sensing elements, i.e., the measured atmosphere pressure. Therefore, the error of the measured atmosphere pressure caused by orientation variation of the pressure sensor can be compensated by deriving the third data value of atmosphere pressure from the first and second data values of atmosphere pressure obtained by the first and second pressure sensing elements.

In a third aspect of the present invention, there is provided an apparatus for detecting a fall of a user, the apparatus comprising:

a pressure sensor configured to obtain a data value of atmosphere pressure for determining whether a fall occurs or not and intended to be worn on the body of the user, the pressure sensor comprising a pressure sensing element being deformable in response to the atmosphere pressure; and a housing configured to house the pressure sensor;

wherein the pressure sensing element comprises an atmosphere pressure sensing surface and the pressure sensor is configured in the housing in a way such that the normal direction of the atmosphere pressure sensing surface is substantially vertical to the gravity direction when the pressure sensor falls to the ground.

Since the normal direction of the atmosphere pressure sensing surface is substantially at right angles to the gravity direction when the pressure sensor falls to the ground, the weight of the pressure sensing element has little effect on the deformation of the pressure sensing element, i.e., the measured atmosphere pressure, and then the error of measured atmosphere pressure caused by improper pressure sensor orientation is almost eliminated.

In a fourth aspect of the present invention, there is provided a method of detecting a fall of a user, the method comprising:

obtaining first and second data values of atmosphere pressure by first and second pressure sensors intended to be worn on the body of the user; and deriving a third data value of atmosphere pressure for determining whether a fall occurs or not from the first and second data values of atmosphere pressure by a processor;

wherein the first and second pressure sensors are configured in a way such that preset orientations of the first and second pressure sensors are opposite to each other.

In a fifth aspect of the present invention, there is provided a method of measuring the atmosphere pressure, the method comprising:

obtaining first and second data values of atmosphere pressure by first and second pressure sensing elements; and deriving a third data value of atmosphere pressure from the first and second data values of atmosphere pressure by a processor;

wherein each pressure sensing element comprises an atmosphere pressure sensing surface which is deformable in response to the atmosphere pressure, and the normal direction of the atmosphere pressure sensing surface of the first pressure sensing element is configured so as to be opposite to the normal direction of the atmosphere pressure sensing surface of the second pressure sensing element.

These and other aspects of the invention will be apparent from and elucidated with reference to the embodiments described hereinafter.

DESCRIPTION OF THE DRAWINGS

The above and other objects and features of the present invention will become more apparent from the following detailed description considered in connection with the accompanying drawings, in which.

The same reference numerals are used to denote similar parts throughout the Figures.

DETAILED DESCRIPTION

Figure 1A:
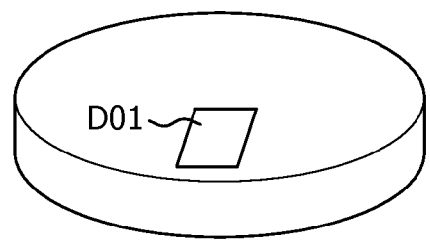
FIG. 1 (*a*) depicts a schematic diagram of a pressure sensor SCP1000-D01 produced by VTI Technologies, and FIG. 1 (*b*) depicts measured altitude values vs real altitude values when the orientation of the pressure sensor varies.
Figure 1B:
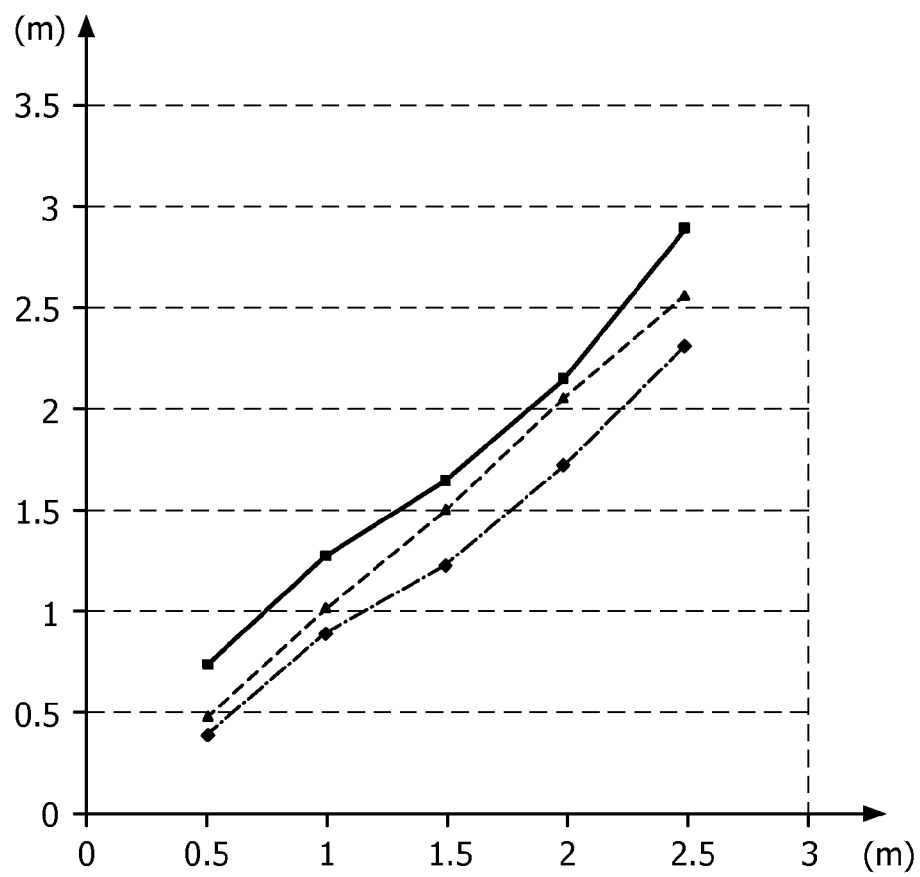
Figure 2A:
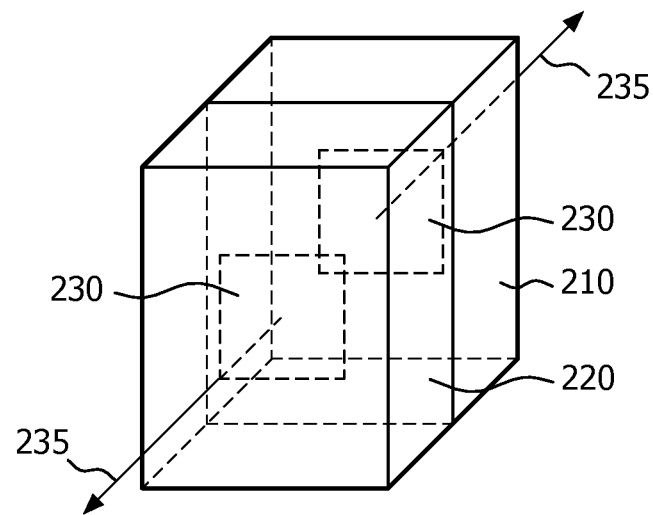
FIG. 2 (*a*) to FIG. 2 (*e*) depict schematic diagrams of embodiments of the first and second pressure sensors.
Figure 2B:
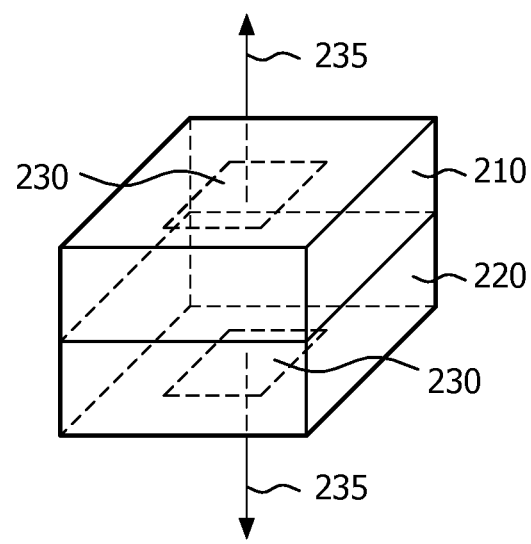
Figure 2C:
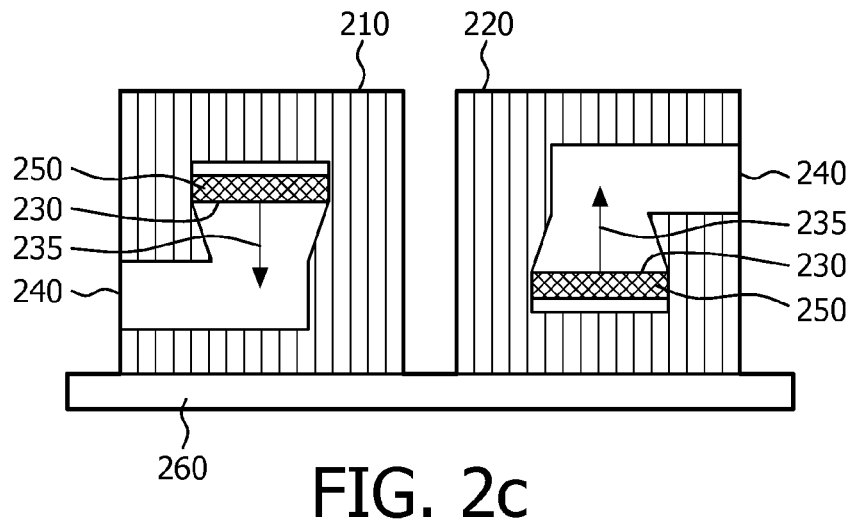
Figure 2D:
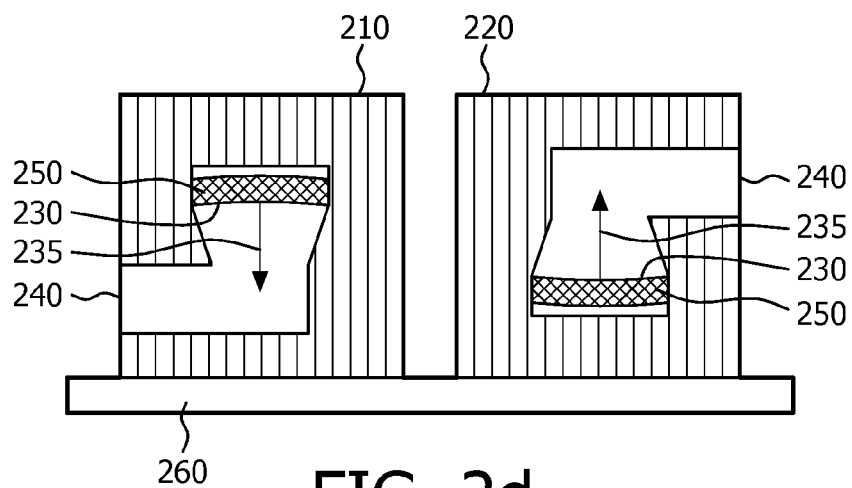
Figure 2E:
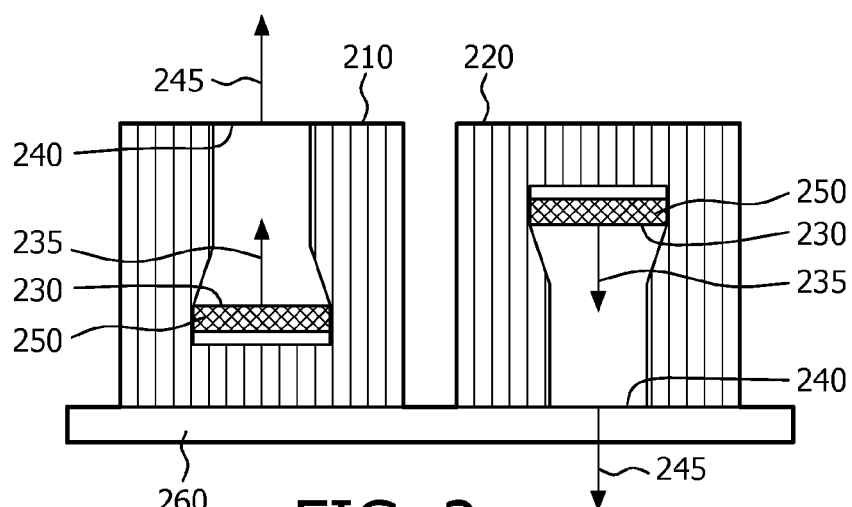

Firstly, there is provided an apparatus for detecting a fall of a user.

The apparatus comprises first and second pressure sensors 210, 220 configured to obtain first and second data values of atmosphere pressure and intended to be worn on the body of the user.

FIG. 2 (*a*) to FIG. 2 (*e*) depict schematic diagrams of embodiments of the first and second pressure sensors 210, 220.

Referring to FIG. 2 (*a*) and FIG. 2 (*b*), the first and second pressure sensors 210, 220 are configured in a way such that preset orientations of the first and second pressure sensors 210, 220 are opposite to each other.

The first and second pressure sensors 210, 220 are of such a kind that their orientations have an effect on the measured atmosphere pressure, i.e., measurement errors are generated due to pressure sensor orientation variations. The reasons for measurement errors due to pressure sensor orientation variation can be manifold: for example, the weight of measuring elements (not shown) comprised in the pressure sensors has an effect on the measured atmosphere pressure.

The first and second pressure sensors 210, 220 can be of the same type having the same appearance and/or structure as shown in FIG. 2 (*a*) and FIG. 2 (*b*), or of different types having different appearances and/or structures.

The preset orientations can be determined in many ways, for example, based on the appearance or the structure of the pressure sensors. If the first and second pressure sensors 210, 220 are of the same type having the same appearance, the preset orientation can be determined according to the appearance of the first and second pressure sensors 210, 220; for example, the preset orientation can be the orientation of the front side of the pressure sensor. If the first and second pressure sensors 210, 220 are different types of pressure sensors, the preset orientation can be determined according to the structure of the first and second pressure sensors 210, 220; for example, the preset orientation can be the orientation of a measuring element comprised in the pressure sensor.

The preset orientations of the first and second pressure sensors 210, 220 are configured so as to be opposite to each other, exerting opposite effects on the data values of atmosphere pressure measured by the first and second pressure sensors 210, 220. For example, the first pressure sensor 210 measures a first data value of atmosphere pressure which is slightly higher than the real data value of atmosphere pressure, and then the second pressure sensor 220 measures a second data value of atmosphere pressure which is slightly lower than the real data value of atmosphere pressure. Therefore, by deriving a third data value of atmosphere pressure for determining whether a fall occurs or not from the first and second data values of atmosphere pressure by a processor (not shown) comprised in the apparatus, a measurement error caused by orientation variation of the apparatus comprising the first and second pressure sensors 210, 220 can be reduced or even eliminated.

The third data value of atmosphere pressure can be derived from the first and second data values of atmosphere pressure in many ways, depending on the effects on the measured atmosphere pressure when orientations of apparatus comprising the pressure sensors 210, 220 are different. For example, if the absolute values of the measurement errors are substantially the same for the atmosphere pressure data value measured by the first and second pressure sensors 210, 220, of which the preset orientations are opposite, the third data value of atmosphere pressure can be derived by calculating the average of the first and second data values of atmosphere pressure. If the absolute values of the measurement errors are not the same for the atmosphere pressure data value measured by the first and the second pressure sensor 210, 220 in opposite orientations, the weight factors of the first and second data values of atmosphere pressure are different for deriving the third data value of atmosphere pressure. The weight factors can be determined in many ways, for example, based on a rule of thumb formula by detecting the orientation of the pressure sensors 210, 220 with accelerometers.

Referring to FIG. 2 (c) to FIG. 2 (e), in an embodiment of the first and second pressure sensors 210, 220, each pressure sensor 210, 220 comprises a pressure sensing element 250 with an atmosphere pressure sensing surface 230, and the orientation is the normal direction 235 of the atmosphere pressure sensing surface 230 of each pressure sensor 210, 220. In this way, if the first and second pressure sensors 210, 220 have different appearances, they can be given opposite preset orientations according to the normal direction 235 of the atmosphere pressure sensing surface 230.

The pressure sensing element 250 is deformable in response to atmosphere pressure. The pressure sensing element 250 can be configured in many ways, for example, it may take the form of an elastic film. The pressure sensing element 250 has two surfaces, one surface facing a vacuum space, and the other being the atmosphere pressure sensing surface 230 facing an atmosphere space which is connected to the outside air via an air entrance 240 through which the atmosphere enters.

When the atmosphere pressure sensing surface 230 is flat as shown in FIG. 2 (c), the normal direction 235 of the atmosphere pressure sensing surface 230 is the direction extending from the pressure sensing element 250 to the atmosphere space and being perpendicular to the atmosphere pressure sensing surface 230. When the atmosphere pressure sensing surface 230 is curved as shown in FIG. 2 (d), the normal direction 235 of the atmosphere pressure sensing surface 230 is the direction extending from the pressure sensing element 250 to the atmosphere space and being perpendicular to the plane tangent to the vertex of the atmosphere pressure sensing surface 230.

Referring to FIG. 2 (e), in another embodiment of the first and second pressure sensors 210, 220, the normal direction 235 of the atmosphere pressure sensing surface 230 is parallel to the normal direction 245 of the air entrance 240. The normal direction 245 of the air entrance 240 is the direction extending from the air entrance 240 to the outside of the pressure sensors 210, 220, and being perpendicular to the plane of the air entrance 240. In this way, the preset orientations of the first and second pressure sensors 210, 220 can be configured so as to be opposite to each other in accordance with the air entrance 240 orientation, which is easy for implementation.

The layout of the first and second pressure sensors 210, 220 can be configured in many ways. For example, the first and second pressure sensors 210, 220 can be closely spaced as shown in FIG. 2 (a) and FIG. 2 (b), or they can be placed with a certain interval between them on a Printed Circuit Board 260 as shown in FIG. 2 (c) to FIG. 2 (d). In addition, the relative position between the first and second pressure sensors 210, 220 and the housing (not shown) covering them is not subject to any limitations.

Figure 3A:
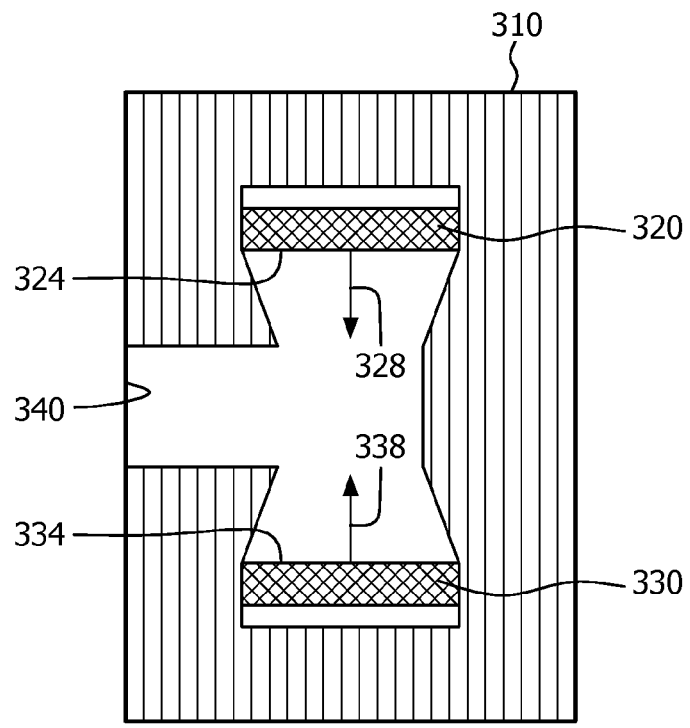
FIG. 3 (*a*) to FIG. 3 (*c*) depict schematic diagrams of embodiments of the first and second pressure sensing elements.
Figure 3B:
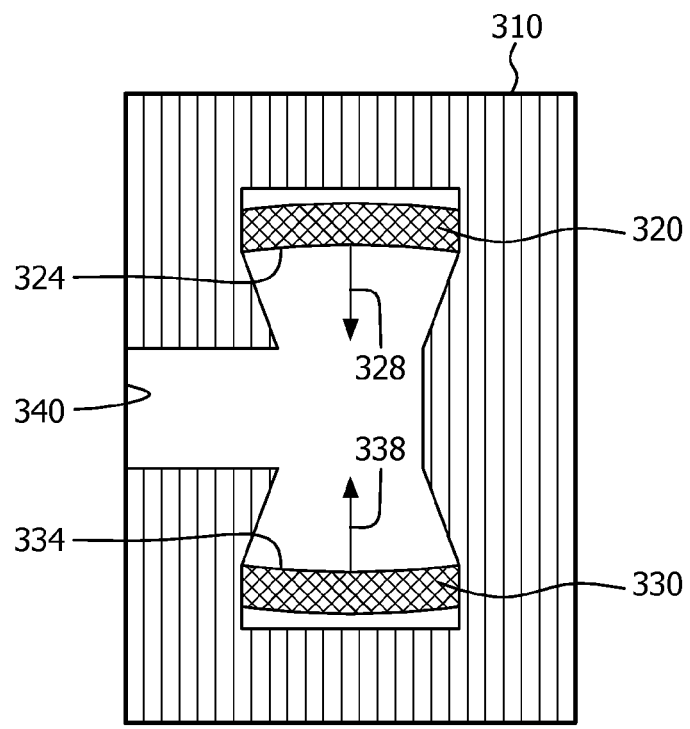
Figure 3C:
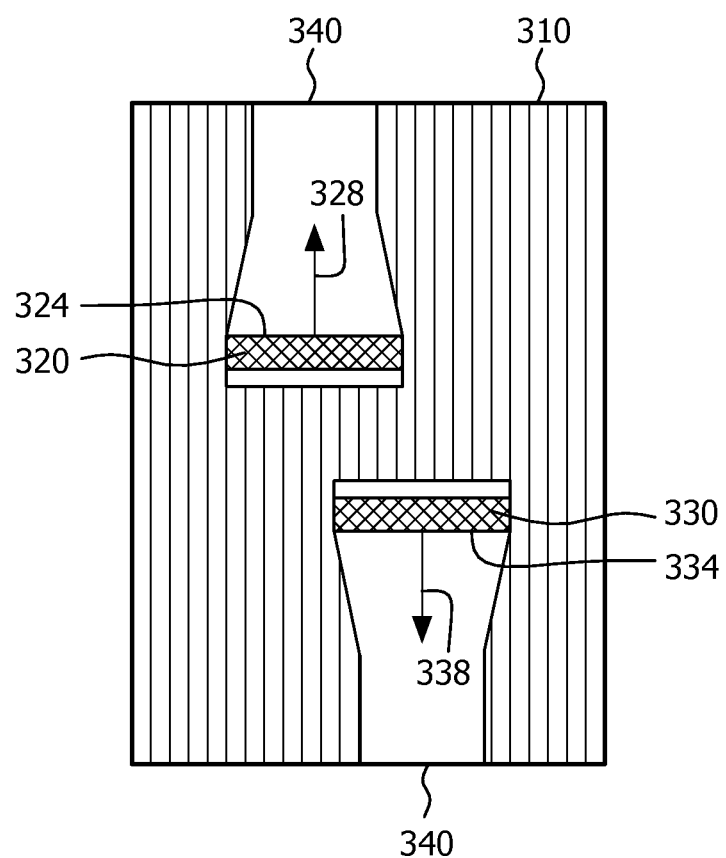
Figure 4A:
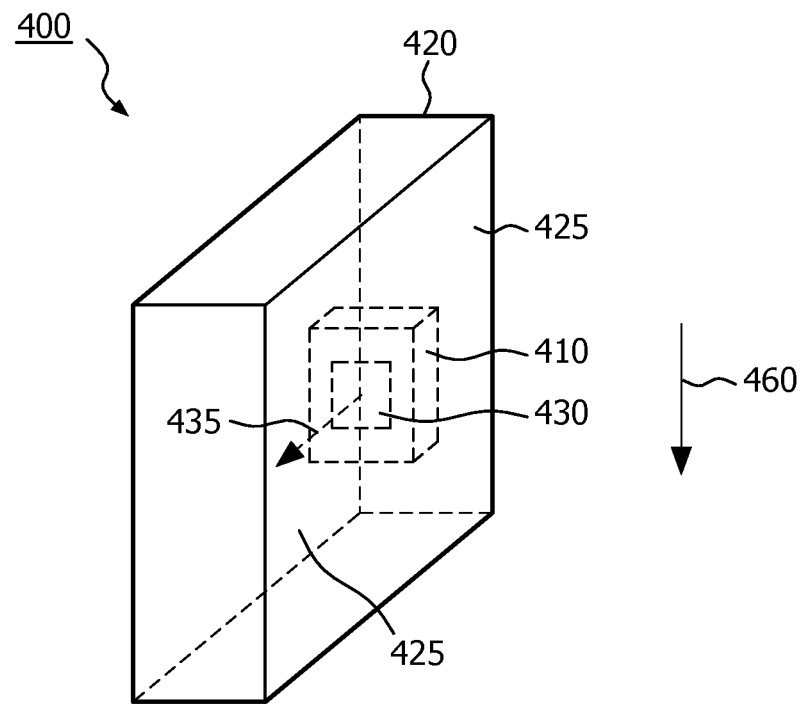
FIG. 4 (*a*) to FIG. 4 (*d*) depict schematic diagrams of embodiments of the fall detecting apparatus comprising a pressure sensor.
Figure 4B:
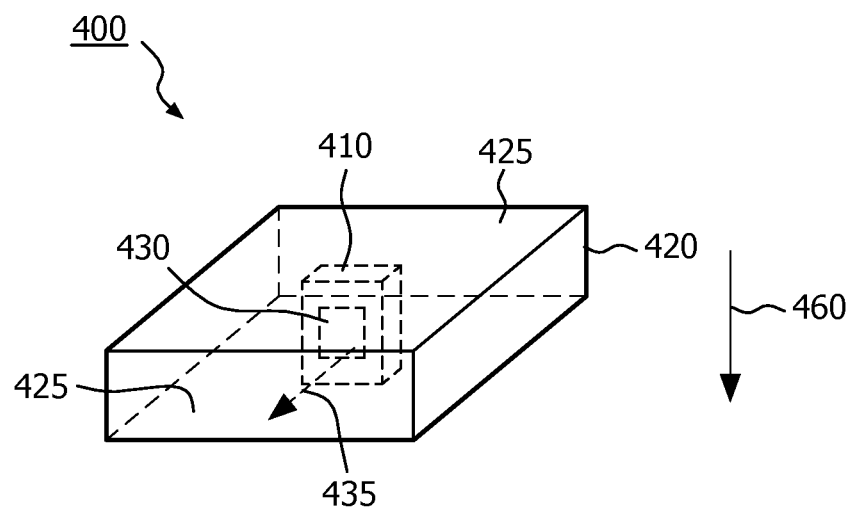
Figure 4C:
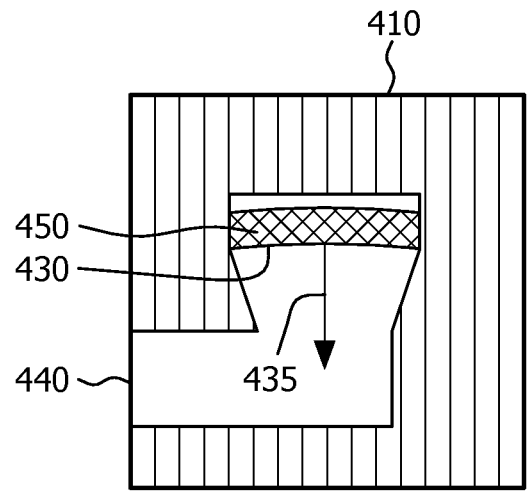
Figure 4D:
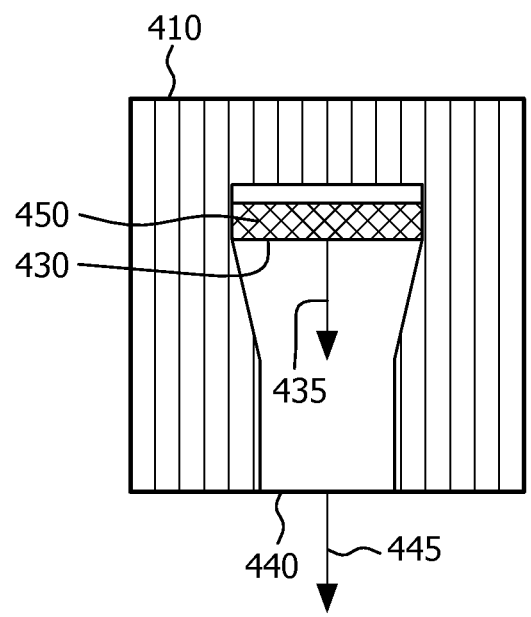

FIG. 3 (a) to FIG. 3 (c) depict schematic diagrams of embodiments of the first and second pressure sensing elements 320, 330.

Secondly, there is provided a pressure sensor 310 for measuring atmosphere pressure.

The pressure sensor 310 comprises first and second pressure sensing elements 320, 330 configured to obtain first and second data values of atmosphere pressure.

Each pressure sensing element 320, 330 is deformable in response to the atmosphere pressure and comprises an atmosphere pressure sensing surface 324, 334, and the normal direction 328 of the atmosphere pressure sensing surface 324 of the first pressure sensing element 320 is configured so as to be opposite to the normal direction 338 of the atmosphere pressure sensing surface 334 of the second pressure sensing element 330, i.e., the atmosphere pressure sensing surfaces 324, 334 of the first and second pressure sensing elements 320, 330 face in opposite directions.

The first and second pressure sensing elements 320, 330 are deformable in response to atmosphere pressure and they can be configured in many ways, for example as an elastic film. The pressure sensing element 320, 330 has two surfaces, one being the surface facing a vacuum space, and the other being the atmosphere pressure sensing surface 324, 334 facing an atmosphere space which is connected to the outside air via an air entrance 340 through which the atmosphere enters.

When the atmosphere pressure sensing surface 324, 334 is flat as shown in FIG. 3 (a) and FIG. 3 (c), the normal direction 328, 338 of the atmosphere pressure sensing surface 324, 334 is the direction extending from the pressure sensing element 320, 330 to the atmosphere space and being perpendicular to the atmosphere pressure sensing surface 324, 334. When the atmosphere pressure sensing surface 324, 334 is curved, as shown in FIG. 3 (b), the normal direction 328, 338 of the atmosphere pressure sensing surface 324, 334 is the direction extending from the pressure sensing element 320, 330 to the atmosphere space and being perpendicular to the plane tangent to the vertex of the atmosphere pressure sensing surface 324, 334.

The pressure sensor 310 further comprises a processor (not shown) configured to derive a third data value of atmosphere pressure from the first and second data values of atmosphere pressure. The third data value of atmosphere pressure can be derived from the first and second data values of atmosphere pressure in many ways. For example, the third data value of atmosphere pressure is derived by calculating an average of the first and second data values of atmosphere pressure.

Since the atmosphere pressure sensing surfaces 324, 334 of the first and second pressure sensing elements 320, 330 face in opposite directions, the weight of the first and second pressure sensing elements 320, 330 have opposite effects on the deformation of the first and second pressure sensing elements, i.e., the first and second data values of atmosphere pressure. Therefore, by deriving the third data value of atmosphere pressure from the first and second data values of atmosphere pressure obtained by the first and second pressure sensing elements 320, 330, there is hardly any measurement error when the orientation of the pressure sensor 310 comprising the first and second pressure sensing elements 320, 330 varies.

The layout of the first and second pressure sensing elements 320, 330 can be configured in many ways. For example, the first and second pressure sensing elements 320, 330 can share the same air entrance 340, as shown in FIG. 3 (a) and FIG. 3 (b), or have separate air entrances 340, as shown in FIG. 3 (c).

FIG. 4 (a) to FIG. 4 (d) depict schematic diagrams of embodiments of a fall detecting apparatus 400 comprising a pressure sensor.

Thirdly, there is provided an apparatus for detecting a fall of a user.

The apparatus 400 comprises a pressure sensor 410 configured to obtain a data value of atmosphere pressure for determining whether a fall occurs or not and intended to be worn on the body of the user. The pressure sensor 410 comprises a pressure sensing element 450 and the pressure sensing element 450 comprises an atmosphere pressure sensing surface 430. The pressure sensing element 450 is deformable in response to atmosphere pressure and can be configured in many ways, for example as an elastic film. The pressure sensing element 450 has two surfaces, one being the surface facing a vacuum space, and the other being the atmosphere pressure sensing surface 430 facing an atmosphere space which is connected to the outside air via an air entrance 440 through which the atmosphere enters.

The apparatus 400 further comprises a housing 420 configured to house the pressure sensor 410. The pressure sensor 410 is configured in the housing 420 in a way such that the normal direction 435 of the atmosphere pressure sensing surface 430 is substantially at right angles to the gravity direction 460 when the pressure sensor 410 falls to the ground.

When the atmosphere pressure sensing surface 430 is flat as shown in FIG. 4 (d), the normal direction 435 of the atmosphere pressure sensing surface 430 is the direction extending from the pressure sensing element 450 to the atmosphere space and being perpendicular to the atmosphere pressure sensing surface 430. When the atmosphere pressure sensing surface 430 is curved as shown in FIG. 4 (c), the normal direction 435 of the atmosphere pressure sensing surface 430 is the direction extending from the pressure sensing element 450 to the atmosphere space and being perpendicular to the plane tangent to the vertex of the atmosphere pressure sensing surface 430.

Since the normal direction 435 of the atmosphere pressure sensing surface 430 is substantially at right angles to the gravity direction 460 when the pressure sensor 410 falls to the ground, the weight of the pressure sensing element 450 has little effect on the deformation of the pressure sensing element 450, i.e., the measured atmosphere pressure. Therefore, the atmosphere pressure measurement error caused by improper pressure sensor 410 orientations is almost eliminated.

Referring to FIG. 4 (a) and FIG. 4 (b), in an embodiment of the apparatus 400, the housing 420 comprises a substantially flat surface 425 and the shape of the housing 420 is substantially flat, and the pressure sensor 410 is configured in the housing 420 in a way such that the normal direction 435 of the atmosphere pressure sensing surface 430 is substantially parallel to the substantially flat surface 425 of the housing 420.

When the apparatus 400 is worn around the neck by a user, as in the way shown in FIG. 4 (a), the normal direction 435 of the atmosphere pressure sensing surface 430 is substantially at right angles to the gravity direction 460. The apparatus 400 falls to the ground when a fall occurs. In most cases, the apparatus 400 will lay on the ground in the way shown in FIG. 4 (b), because the housing 420 is flat. The normal direction 435 of the atmosphere pressure sensing surface 430 is substantially parallel to the substantially flat surface 425 of the housing 420, therefore the normal direction 435 of the atmosphere pressure sensing surface 430 is still substantially at right angles to the gravity direction 460 when the pressure sensor 410 falls to the ground. So, the weight of the pressure sensing element 450 does not affect the deformation of the pressure sensing element 450. In this way, the pressure sensor 410 comprised in the apparatus 400 can measure the atmosphere pressure correctly when the apparatus 400 is worn around the neck or when the apparatus 400 falls to the ground.

Referring to FIG. 4 (d), in an embodiment of the pressure sensor 410, the normal direction 435 of the atmosphere pressure sensing surface 430 is parallel to the normal direction 445 of the air entrance 440. The normal direction 445 of the air entrance 440 is the direction extending from the air entrance 440 to the outside of the pressure sensor 410, and being perpendicular to the plane of the air entrance 440. In this way, the pressure sensors 410 can be configured in the housing 420 in accordance with the orientation of the air entrance 440, which is easy for implementation.

The housing 420 is designed to guarantee that the normal direction 435 of the atmosphere pressure sensing surface 430 is substantially at right angles to the gravity direction 460 when the pressure sensor 410 falls to the ground. The flat housing 420 can have many shapes. For example, the housing 420 can be in the shape of a cuboid, as shown in FIG. 4 (a) and FIG. 4 (b).

Figure 5A:
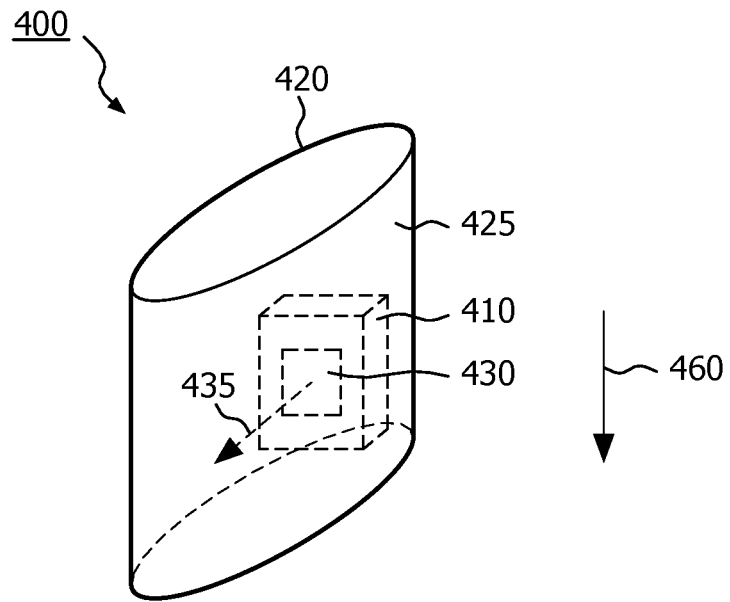
FIG. 5 (*a*) and FIG. 5 (*b*) depict schematic diagrams of one embodiment of the shape of the housing comprised in the fall detecting apparatus comprising a pressure sensor.
Figure 5B:
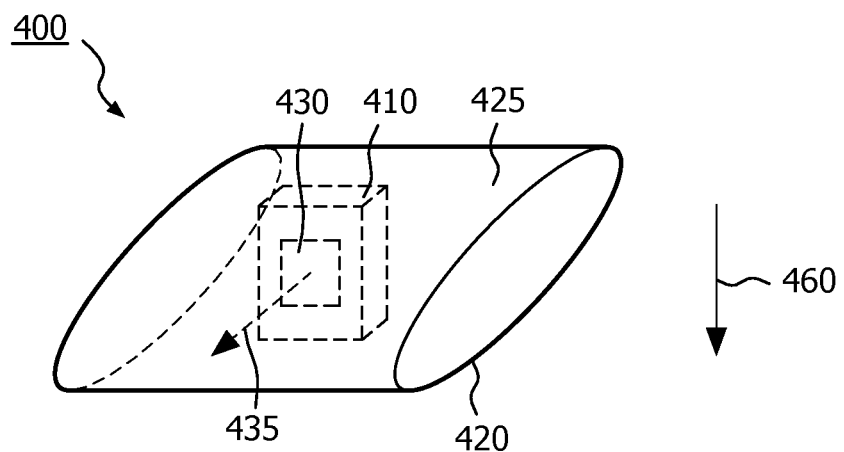

FIG. 5 (a) and FIG. 5 (b) depict schematic diagrams of an embodiment of the shape of the housing 420 comprised in the fall detecting apparatus 400 comprising a pressure sensor 410. The flat housing 420 is in the shape of an ellipse. In this case, the configuration in which the normal direction 435 of the atmosphere pressure sensing surface 430 is substantially parallel to the substantially flat surface 425 of the housing 420 is artificially defined as a configuration in which the normal direction 435 of the atmosphere pressure sensing surface 430 is substantially parallel to a plane tangent to the vertex of the substantially flat surface 425.

Figure 6A:
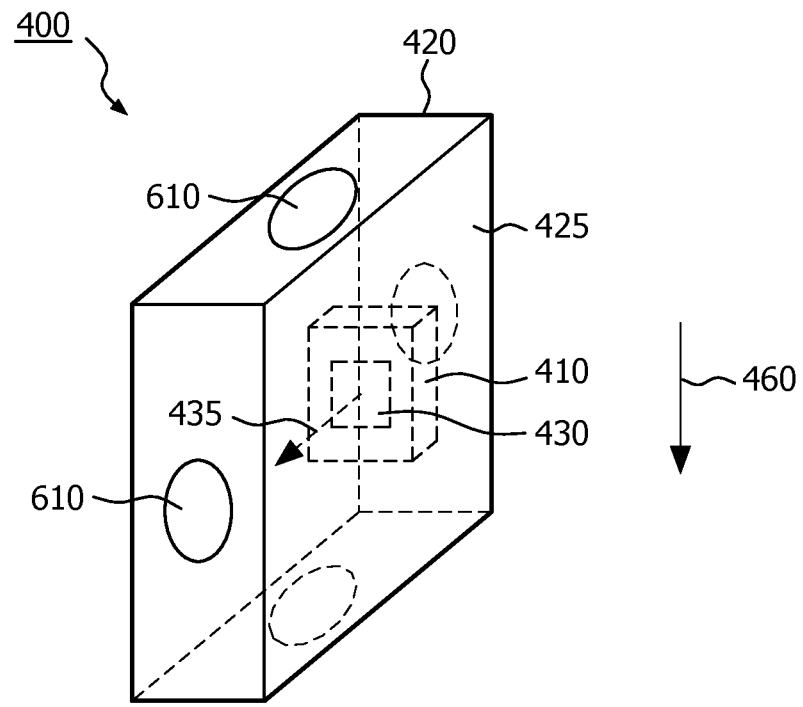
FIG. 6 (*a*) to FIG. 6 (*c*) depict schematic diagrams of another embodiment of the shape of the housing comprised in the fall detecting apparatus comprising a pressure sensor.
Figure 6B:
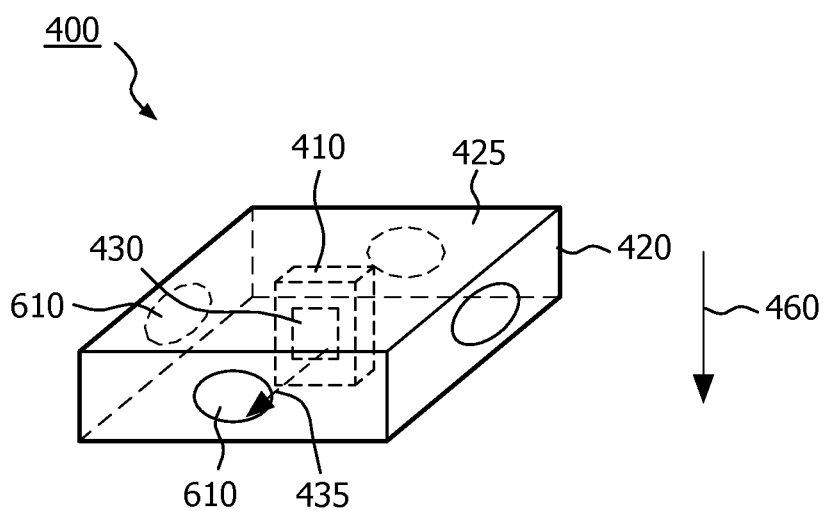
Figure 6C:
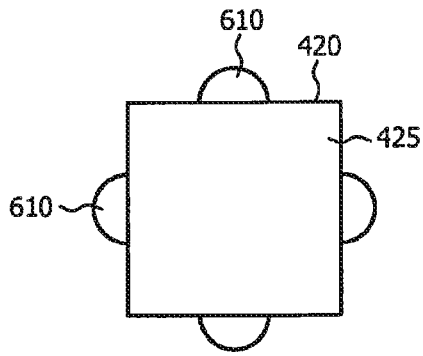

FIG. 6 (a) to FIG. 6 (c) depict schematic diagrams of another embodiment of the shape of the housing 420 comprised in the fall detecting apparatus 400 comprising a pressure sensor 410. FIG. 6 (c) is the view of the apparatus 400 in FIG. 6 (a) and FIG. 6 (b) as seen from the surface 425. A plurality of convex surfaces 610 are provided on the side surfaces of the housing 420 to guarantee that the apparatus 400, when a fall occurs, will lay on the ground in most cases in the way shown in FIG. 6 (b).

Figure 7:
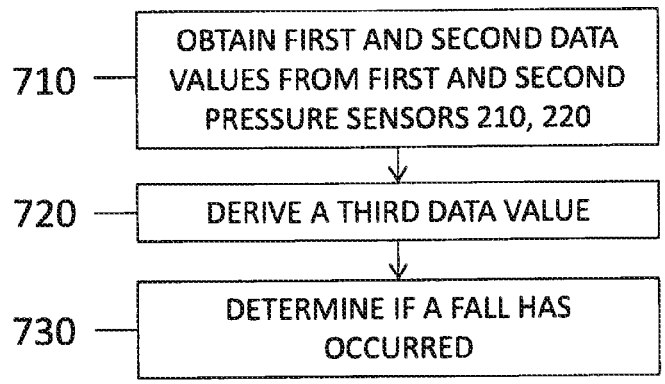
FIG. 7 is a flowchart illustrating an embodiment of the method of detecting a fall of a user.

FIG. 7 is a flowchart illustrating an embodiment of the method of detecting a fall of a user.

Referring to FIG. 7, the method comprises a step 710 of obtaining first and second data values of atmosphere pressure by first and second pressure sensors 210, 220 intended to be worn on the body of the user. The first and second pressure sensors 210, 220 are configured in a way such that preset orientations of the first and second pressure sensors 210, 220 are opposite to each other.

The method further comprises a step 720 of deriving a third data value of atmosphere pressure data for determining whether a fall occurs or not from the first and second data values of atmosphere pressure by a processor. Optionally, the method may include a step 730 of determining if has occurred.

In an embodiment of the method, each pressure sensor 210, 220 comprises a pressure sensing element 250 with an atmosphere pressure sensing surface 230, and the preset orientation is the normal direction 235 of the atmosphere pressure sensing surface 230 of each pressure sensor 210, 220.

In another embodiment of the method, each pressure sensor 210, 220 comprises an air entrance 240 through which the atmosphere enters, and the normal direction 235 of the atmosphere pressure sensing surface 230 is parallel to the normal direction 245 of the air entrance 240.

In a further embodiment of the method, the step 720 of deriving comprises a sub-step of deriving the third data value of atmosphere pressure by calculating the average of the first and second data values of atmosphere pressure by the processor.

Figure 8:
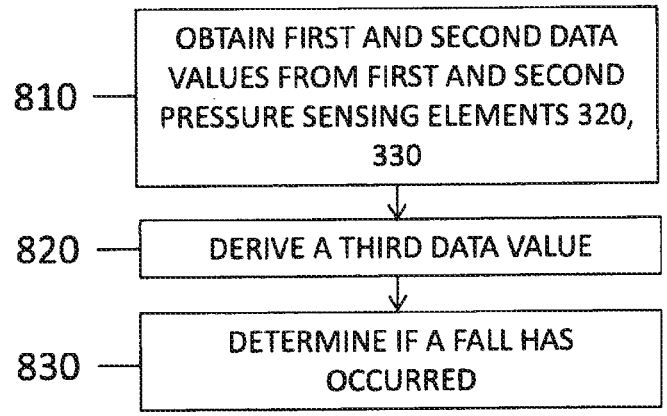
FIG. 8 is a flowchart illustrating an embodiment of the method of measuring the atmosphere pressure.

FIG. 8 is a flowchart illustrating an embodiment of the method of measuring the atmosphere pressure.

Referring to FIG. 8, the method comprises a step 810 of obtaining first and second data values of atmosphere pressure by first and second pressure sensing elements 320, 330. Each pressure sensing element 320, 330 comprises an atmosphere pressure sensing surface 324, 334 which is deformable in response to the atmosphere pressure, and the normal direction 328 of the atmosphere pressure sensing surface 324 of the first pressure sensing element 320 is configured so as to be opposite to the normal direction 338 of the atmosphere pressure sensing surface 334 of the second pressure sensing element 330.

The method further comprises a step 820 of deriving a third data value of atmosphere pressure from the first and second data values of atmosphere pressure data by a processor. Optionally, the method may include a step 830 of determining if a fall has occurred.

It should be noted that the above-mentioned embodiments illustrate rather than limit the invention and that those skilled in the art would be able to design alternative embodiments without departing from the scope of the appended claims. In the claims, any reference signs placed between parentheses shall not be construed as limiting the claim. The word "comprising" does not exclude the presence of elements or steps not listed in a claim or in the description. The word "a" or "an" preceding an element does not exclude the presence of a plurality of such elements. In the apparatus claims enumerating several units, several of these units can be embodied by one and the same item of hardware or software. The usage of the words first, second and third, et cetera, does not indicate any ordering. These words are to be interpreted as names.

What is claimed is:

1. An apparatus for detecting a fall of a user, the apparatus comprising:
    first and second pressure sensors configured to obtain first and second data values of atmosphere pressure; and
    a processor configured to derive, from the first and second data values of atmosphere pressure, a third data value of atmosphere pressure indicating a change in altitude indicative of a fall;
    wherein the first and second pressure sensors are configured in a way such that preset orientations of the first and second pressure sensors are opposite to each other.

2. The apparatus as claimed in claim 1, wherein the third data value of atmosphere pressure is derived by calculating the average of the first and second data values of atmosphere pressure.

3. The apparatus as claimed in claim 1, wherein the third data value of atmosphere pressure is derived by calculating weight values assigned to the first and second data values of atmosphere pressure.

4. The apparatus as claimed in claim 3, wherein the weight values are determined based on an orientation of the first and second pressure sensors.

5. The apparatus as claimed in claim 1, wherein each pressure sensor comprises a pressure sensing element with an atmosphere pressure sensing surface, surface and the preset orientation is the normal direction of the atmosphere pressure sensing surfaces of each pressure sensor.

6. The apparatus as claimed in claim 5, wherein each pressure sensor comprises an air entrance through which the atmosphere enters, and the normal direction of the atmosphere pressure sensing surface is parallel to the normal direction of the air entrance.

7. The apparatus as claimed in claim 5, wherein each pressure sensor comprises an air entrance through which the atmosphere enters, and the normal direction of the atmosphere pressure sensing surface is perpendicular to the normal direction of the air entrance.

8. A pressure sensor (or measuring atmosphere pressure, the pressure sensor comprising:
    first and second pressure sensing elements configured to obtain first and second data values of atmosphere pressure; and
    a processor configured to derive a third data value of atmosphere pressure from the first and second data values of atmosphere pressure;
    wherein each pressure sensing element is deformable in response to the atmosphere pressure and comprises an atmosphere pressure sensing surface, and the normal direction of the atmosphere pressure sensing surface of the first pressure sensing element is configured so as to be opposite to the normal direction of the atmosphere pressure sensing surface of the second pressure sensing element.

9. An apparatus for detecting a fall of a user, the apparatus comprising:
    a pressure sensor configured to obtain a data value of atmosphere pressure, the pressure sensor comprising a pressure sensing element being deformable in response to the atmosphere pressure; and
    a housing configured to house the pressure sensor;
    wherein the pressure sensing element comprises an atmosphere pressure sensing surface and the pressure sensor is configured in the housing in a way such that the normal direction of the atmosphere pressure sensing surface is substantially at right angles to the gravity direction when the pressure sensor falls to the ground.

10. The apparatus as claimed in claim 9 wherein the housing comprises a plurality of convex surfaces.

11. The apparatus as claimed in claim 9 wherein the housing comprises six flat sides and one convex surface is formed on four of the six flat sides.

12. The apparatus as claimed in claim 9, wherein the housing comprises a substantially flat surface and the shape of the housing is substantially flat, and the pressure sensor is configured in the housing in a way such that the normal direction of the atmosphere pressure sensing surface is substantially parallel to the substantially flat surface of the housing.

13. The apparatus as claimed in claim 12, wherein the pressure sensor comprises an air entrance through which the atmosphere enters, and the normal direction of the atmosphere pressure sensing surface is parallel to the normal direction of the air entrance.

14. The apparatus as claimed in claim 9 wherein the housing comprises an elliptical portion and a flat portion.

15. The apparatus as claimed in claim 14 wherein the normal direction of the atmosphere pressure sensing surface is parallel to the flat portion.

16. A method of detecting a fall of a user, the method comprising:
    obtaining first and second data values of atmosphere pressure by first and second pressure sensors; and deriving a third data value of a atmosphere pressure from the first and second data values of atmosphere pressure by a processor;

wherein the first and second pressure sensors are configured in a way such that preset orientations of the first and second pressure sensors are opposite to each other.

17. The method as claimed in claim 16, wherein the step of deriving comprises:

deriving the third data value of atmosphere pressure by calculating the average of the first and second data values of atmosphere pressure by the processor.

18. The method as claimed in claim 16, wherein each pressure sensor comprises a pressure sensing element with an atmosphere pressure sensing surface, and the preset orientation is the normal direction of the atmosphere pressure sensing surface of each pressure sensor.

19. The method as claimed in claim 18, wherein each pressure sensor comprises an air entrance through which the atmosphere enters, and the normal direction of the atmosphere pressure sensing surface is parallel to the normal direction of the air entrance.

20. A method of measuring the atmosphere pressure, the method comprising:

obtaining first and second data values of atmosphere pressure by first and second pressure sensing elements; and deriving a third data value of atmosphere pressure from the first and second data values of atmosphere pressure by a processor;

wherein each pressure sensing element comprises an atmosphere pressure sensing surface which is deformable in response to the atmosphere pressure, and the normal direction of the atmosphere pressure sensing surface of the first pressure sensing element is configured so as to be opposite to the normal direction of the atmosphere pressure sensing surface of the second pressure sensing element.

* * * * *